United States Patent
Chien

(10) Patent No.: US 10,505,326 B2
(45) Date of Patent: Dec. 10, 2019

(54) MULTIPLE FUNCTIONS WALL COVER PLATE HAS BUILT-IN USB AND LIGHT MEANS

(71) Applicant: Tseng-Lu Chien, Walnut, CA (US)

(72) Inventor: Tseng-Lu Chien, Walnut, CA (US)

( * ) Notice: Subject to any disclaimer, the term of this patent is extended or adjusted under 35 U.S.C. 154(b) by 0 days.

(21) Appl. No.: 14/817,675

(22) Filed: Aug. 4, 2015

(65) Prior Publication Data
US 2015/0340826 A1 Nov. 26, 2015

Related U.S. Application Data

(63) Continuation-in-part of application No. 13/910,295, filed on Jun. 5, 2013, now Pat. No. 9,732,921.

(51) Int. Cl.
| | |
|---|---|
| *H01R 27/02* | (2006.01) |
| *H01R 13/66* | (2006.01) |
| *H01R 13/70* | (2006.01) |
| *H01R 13/717* | (2006.01) |
| *H01R 13/73* | (2006.01) |

(52) U.S. Cl.
CPC ........... *H01R 27/02* (2013.01); *H01R 13/665* (2013.01); *H01R 13/70* (2013.01); *H01R 13/7175* (2013.01); *H01R 13/73* (2013.01)

(58) Field of Classification Search
None
See application file for complete search history.

(56) References Cited

U.S. PATENT DOCUMENTS

| | | | | |
|---|---|---|---|---|
| 7,318,653 B2* | 1/2008 | Chien | .................... | F21S 8/035 362/95 |
| 7,862,350 B2* | 1/2011 | Richter | .................. | H01H 9/182 362/95 |
| 8,758,031 B2* | 6/2014 | Cheng | ..................... | H05K 5/02 439/107 |
| 2008/0012423 A1* | 1/2008 | Mimran | ............... | H01R 25/003 307/11 |
| 2008/0140565 A1* | 6/2008 | DeBenedetti | .......... | G06Q 20/10 705/39 |
| 2009/0315509 A1* | 12/2009 | Wu | ......................... | H01R 27/02 320/107 |
| 2012/0276763 A1* | 11/2012 | Quezada | .............. | H01R 13/665 439/108 |
| 2012/0292991 A1* | 11/2012 | Dodal | ..................... | H02H 3/16 307/11 |

* cited by examiner

*Primary Examiner* — Elmito Breval
(74) *Attorney, Agent, or Firm* — Bacon & Thomas, PLLC

(57) ABSTRACT

A multiple function wall cover plate has a built-in USB charger and light connected by prongs to an existing wall outlet's inner receptacle to supply AC power source to the multiple function wall cover's circuit(s) and drive each circuit to carry out predetermined functions. The wall outlet may also have functions in addition to the USB charging and light functions. A movable piece may be provided to adapt the wall outlet to inner receptacles having oval-shaped and rectangular-shaped outlets.

12 Claims, 9 Drawing Sheets

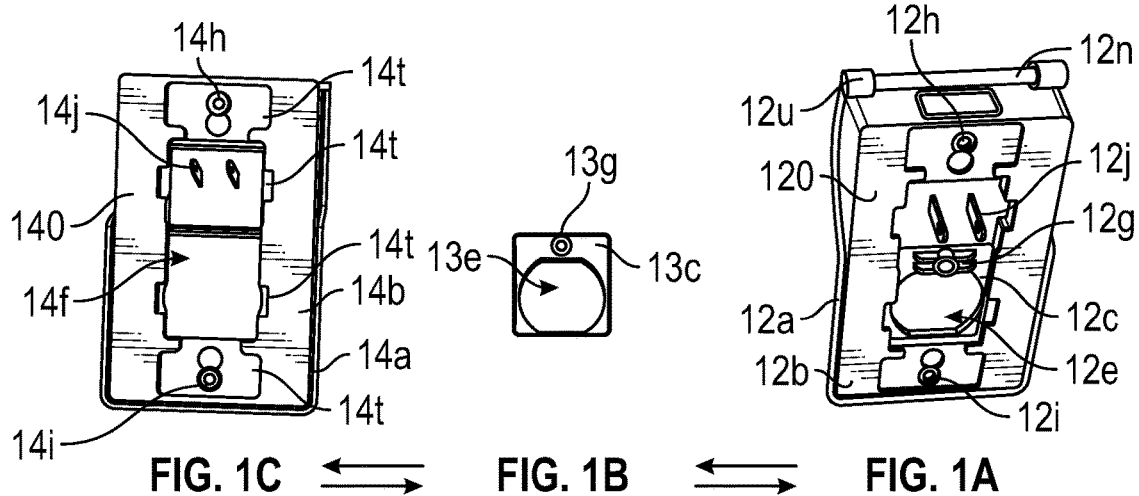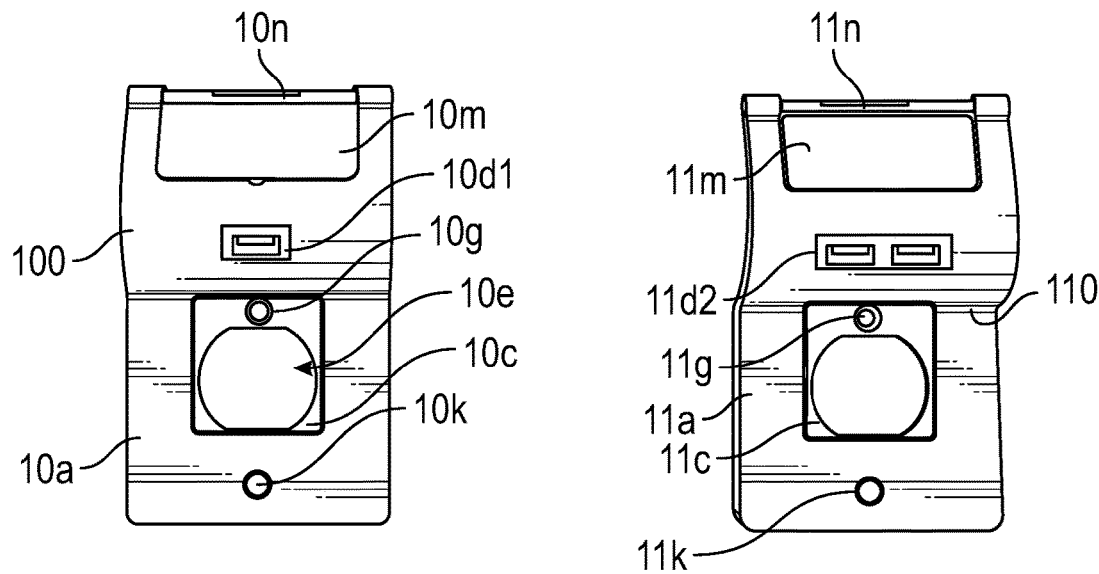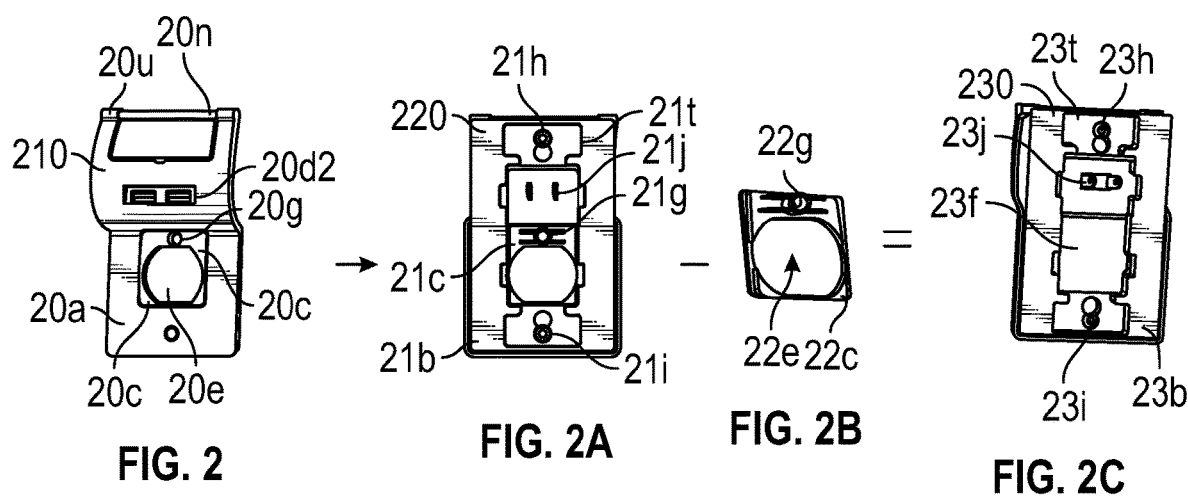

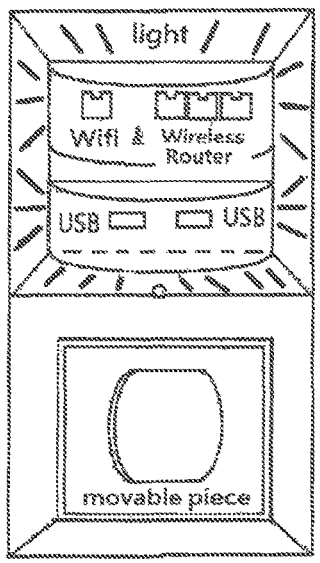
FIG. 16
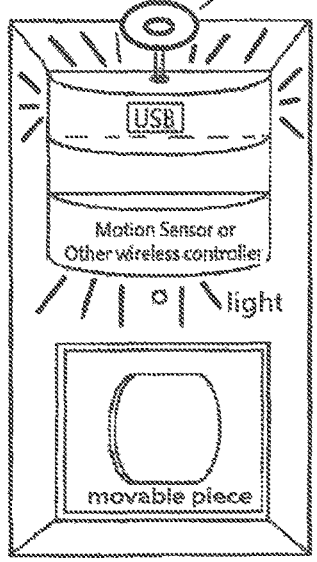
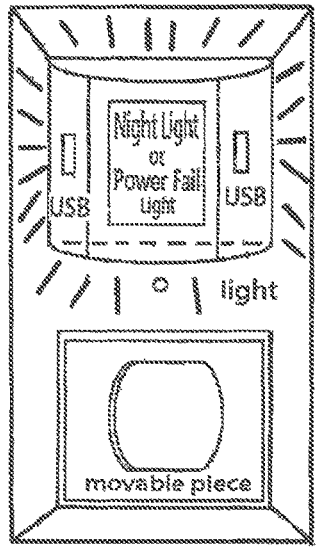
FIG. 17
FIG. 18
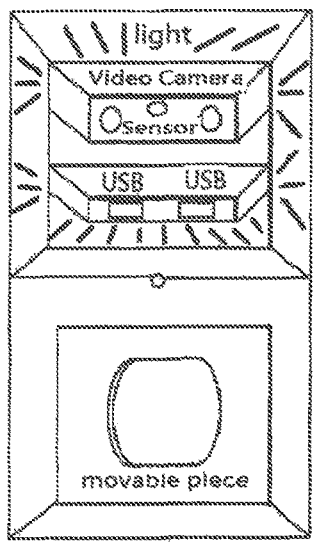
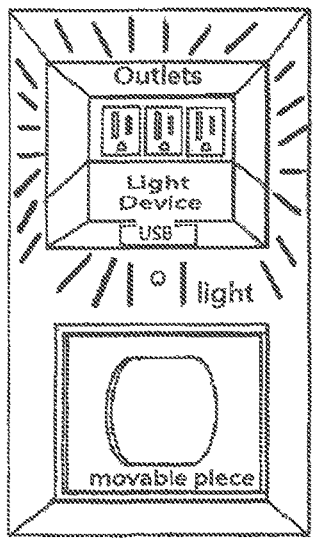
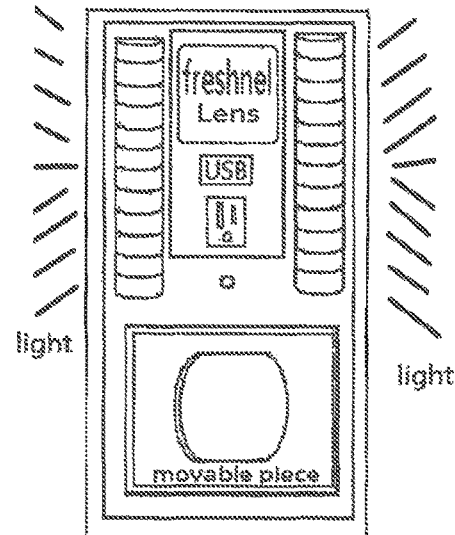
FIG. 19
FIG. 20
FIG. 21

MULTIPLE FUNCTIONS WALL COVER PLATE HAS BUILT-IN USB AND LIGHT MEANS

This application is a continuation-in-part of U.S. patent application Ser. No. 13/910,295, filed Jun. 5, 2013.

BACKGROUND OF THE INVENTION

This application has subject matter in common with the inventors' U.S. Pat. No. 7,318,653, which discloses built-in outlets and light means on a wall plate cover.

The current invention is related to the USB charger related products having a built-in liquid and display unit disclosed in the inventor's U.S. Pat. Nos. 5,926,440 and 7,909,477, in which the display unit is filed with a liquid containing medium-means, decorative-means, or miniature-means and which may utilize a variety of different light source means.

The current application also has subject matter in common with the inventor's U.S. patent application Ser. No. 13/870,253, filed Apr. 22, 2013, which is directed to a wire arrangement for hand-reachable desktop USB charger related products.

The current application also has subject matter in common with the inventor's U.S. patent application Ser. No. 13/863,073, filed Apr. 15, 2013, which discloses a power station or products having built-in USB and LED units for desk top installation.

The current application also has subject matter in common with the inventor's U.S. patent application Ser. No. 13/858,046, filed Apr. 8, 2013, which discloses a wire arrangement for a USB charger device having an add-on or built-in wire arrange-means.

The current application also has subject matter in common with U.S. patent application Ser. No. 13/161,643, filed May 27, 2011, which discloses a desk top LED device having a USB unit to charge other electric or digital data devices.

The current application also has subject matter in common with U.S. patent application Ser. No. 13/117,227, filed May 27, 2011, which discloses a universal module for a USB unit and/or outlet-unit for electric or digital data devices.

The current application also has subject matter in common with U.S. patent application Ser. No. 12/950,017, which discloses a multiple surface LED light having USB outlets, AC outlets, and/or LEDs.

The desktop hand-reachable USB-charger related products disclosed in the above-listed applications of the inventor may include built-in wire-arrangements so that wires for receiving-means such as USB-ports, outlets, receiving socket, LED-units, or any combinations thereof may be stored in a way that offers h more convenience to people.

Main features of the arrangements described in the above-listed applications of the inventor, which may be adapted for use in connection with the current invention, include:

1. A USB charger and light means may be installed within a multiple cover plate so as to make the device thinner and more compact than a plug-in type overlay for an existing wall cover plate.

2. A built-in wire arrangement may be provided to coil, wrap, roll, store, and release an AC power wire or other wires related to the USB charger operation so as to eliminate mess as described in the inventor's copending U.S. patent application Ser. No. 13/858,046.

3. The basic model may have, in addition to a built-in USB charger, a built-in light means selected from market available light means to not only charge other electric or digital data devices but also to offer a light means for illumination. The light means is preferably an LED light means such as the numerous LED light means described in the inventor's prior patents and publications, including LED light means with more than one LED, more than one optics means, more than one function, more than one reflective means, and other features to enable the LED light means to have the best light performance.

4. Optionally, the USB charger and light means can be take the form of a flat or thin product with a big size that can underlay all or at least one of an existing power strip with a built-in plurality of outlets to offer people more outlets and receiving means to connect more external electric or digital data devices.

5. The USB charger output-end power may have a minimum of 1.0 Amp which is more than is typically provided by laptop USB ports or other portable or travel USB chargers. As a result, there is no need for a long wait time to charge electric or electronic devices.

6. The wire arrangement may include a roller, retractable means, spring means, or twist means to allow people to keep all charging related wires or AC power wires well stored well and not make a mess.

The present invention may utilize features of the inventor's U.S. patent application Ser. No. 10/954,189, filed Oct. 1, 2004, now abandoned, which disclose an electro-luminescent wall cover plate.

The current invention adds a movable-piece to a wall outlet cover to enable the wall outlet cover to fit different kinds and different styles of wall inner receptacle kits, the majority of which include one of the following two configurations: (A) 2 oval-shape receptacles with a center screw hole, and (B) 1 rectangular-shape receptacle without a central screw hole but with top and lower screw holes. The movable-piece is added for type (A) receptacles removed for type (B) receptacles. The current invention's wall cover will therefore become a universal wall cover to fit the most common different types of wall inner receptacle. However, the current invention can also take the form of a non-universal wall cover for type (A) or type (B) only. It will be appreciated that any wall cover having a built-in USB charger may fall within the scope of the current invention.

The above-discussed wire arrangement may be implemented by an added-on elastic means or a built-in groove, frame, hook, or groove arranged to fit the charging wires of a USB charger, electric device, iPhone, iPad, digital device, consumer electric device, communication device, or computer device, with one end of the wire including a USB-plug to insert into the USB charger's receiving ports.

The current invention provides improvements to the inventor's prior multiple function wall cover plate, and in particular a wall cover having a built-in light source and receiving-means including any combination of a USB charger, AC power source, and optional other electric devices.

A multiple function wall cover plate has been disclosed in several prior patents, including U.S. Pat. Nos. 6,714,725, 6,810,204, 6,832,794, and 6,839,506, but the prior multiple function wall cover plates have a relatively thick housing and are very dangerous to children because the chemical refill can easily be removed. The current invention uses a screw to securely lock all components and prevent children from touching the chemical containing components. In addition, whereas the thicker body of the prior multiple function wall cover plates are too ugly because the multiple function components are added-on to the existing wall cover plate (rather than replace it), the current invention's concept is to replace the existing wall cover plate so that the thickness will be much less than that of the prior art. In particular, the current invention uses a conventional commercially available refill component which has the dimensions 6.5 cm length by 3.5 cm width by 0.8 cm height and is simply installed on the back housing to reduce thickness and improve appearance.

The inventor's prior art also includes light devices that incorporate (1) an air freshener, and (2) a nightlight, which may include an electro-luminescent (E.L.) element, LED, incandescent light, fiber optics, a fluorescent light, or a black tube, and related circuitry for the light source, and (3) a receptacle arrangement (which may include any number of receptacles) to let the wall cover plate offer the best functions to consumers. But the inventor's prior art wall plates lack of a USB charger, which is a main function for the present application. The current invention also has a super compact USB charger circuit in a (Aa) USB-unit, (Ab) USB-module, or (Ac) sealed-unit or (Ad) universal module such as the ones described in the inventor's U.S. patent application Ser. Nos. 12/161,643, 12/117,227, 12/950,017, and 14/105,607, which disclose desk top items having a USB unit or USB module to charge other electric devices and digital devices.

The current invention offers people more convenience by enabling them to charge their electric device or digital data device from a built-in wall cover. Other USB chargers are not permanently installed on a wall. The USB charger needs a special circuit to change the input AC current into DC current, which is not needed for the wall outlet cover described in the inventor's U.S. Pat. No. 7,318,653, so this is brand new and different concept and requires different technical skills and construction.

Other prior art includes U.S. Pat. Nos. 6,716,256; 6,657, 380; 6,642,452; 6,413,598; 6,388,345; 6,342,995; 6,089, 893; 6,086,211; 6,050,716; 5,934,451; 5,899,549; 5,842, 763; 5,683,166; 5,670,776; 5,660,459; 5,637,930; 5,586, 879; 5,544,025; 5,485,356; 5,407,721; 5,117,734; 4,924, 349; 4,774,641; 4,755,913; 4,739,187; 4,617,613; 4,546, 419; 4,514,789; 4,255,780; 4,240,090; 4,038,582; and 3,895,225, as well as the Inventor's prior U.S. Pat. Nos. 6,280,053; 6,171,117; 6,170,958; and 6,183,101. None of these prior art patents discloses a multiple function wall cover plate having a plurality of functions including (1) fragrance(s), (2) receptacle(s), and (3) nightlight(s) to easily replace the original wall outlet's cover plate and provide electricity delivery from the prongs of the multiple function wall cover plate, and in particular, a multiple function wall cover plate having a plurality of functions and which nevertheless has the shape and thickness of an existing wall outlet and a safety screw to prevent children from touching any parts of a refill, the nightlight, or the receptacle.

The inventor's prior art mainly teaches a multiple function wall cover which has (1) outlets, and (2) a light device and other functions (but not a USB charger) including the following features:

(1) An air fragrance feature, the wall cover having
at least one ventilation area to allow the inside refill's fragrance to be spread out to the environment;

(2) A light source feature in which the wall cover includes
at least one nightlight area that incorporates a light source which may be selected from an electro-luminescent (EL) element, an LED, an incandescent light, a neon light, a fluorescent tube, a black tube, a gas filled light source, or any equivalent light source to offer a nightlight function;

(3) An outlet feature in which the
multiple function wall cover plate includes at least one pair of receptacles to keep the existing wall outlet functions without reducing the number of receptacles while adding multiple functions to the wall cover plate;

(4) The openings for scent or light emit
may include alternative openings, grills, windows, cutouts to allow the scent or smell of the refill to spread out quickly and also can allow the light means to emit light out to a viewer;

(5) The multiple function wall cover plate may have a center
screw hole (18) to allow the multiple function wall cover plate to be securely fastened by a screw though the original outlet's screw hole and replace the original outlet's wall cover plate;

(6) The multiple function wall cover plate also may have at
least one pair of prong sets which can be easily inserted into the original wall outlet's receptacle and supply electricity from the original wall outlet to the multiple function wall cover plate's receptacle or receptacle(s).

The current invention includes a USB charger unit having its own input AC current and a current conversion circuit for converting an AC input current into DC current. Unlike the inventor's prior wall outlet cover, which added AC-outlets to provide people with more outlets than the replaced wall cover, increasing the 1 or 2 outlets of the replaced wall cover to get power with 2, 3, or 4 outlets. The current invention offers any number of USB related chargers to charge all device(s) having internal energy storage, such as rechargeable batteries or capacitors. In the prior art, only a conductive metal piece is required to supply electricity to each added outlet, whereas in the current invention, the USB charger needs a lot of electric components, such as a transformer, inverter, capacitor, resistor, and so forth to change the AC input current from prongs into a DC output current.

Unlike the inventor's prior wall outlet cover, in which light is emitted out from a housing side surface having an opening, hole, or grill, and which is therefore not for use as an emergency light, power fail light, motion sensor light, or remote control light that offers illumination to people over a large areas, The current invention provides a light arrangement on a front side of the wall outlet cover.

Unlike the inventor's prior wall outlet cover, the current invention does not need an extra circuit for the LED light sources because the built-in USB charger already provides a DC power source that can directly offer power to any number of LEDs.

In contrast to the inventor's prior wall outlet cover, the current invention provides for the wall outlet cover to be fastened to the outlet inner kit or receptacle by either a center screw or top and lower screw holes.

The current invention has movable-piece that can fit for all kinds of different inner kits (e.g., an inner receptacle for 2 oval-shaped outlets or 1 rectangular-shaped outlet) so that the wall outlet cover of the current invention can fit all kinds of market available inner kits and not just those with a center screw as in the inventor's prior wall outlet. This is big improvement because it ensures that the consumer will never buy a wrong wall outlet cover.

The current invention has a shape and movable-piece construction that, unlike the inventor's prior wall outlet cover, provides a universal wall outlet cover for all market-available inner receptacle shapes.

Also, the current invention differs from other U.S. prior art, as follows: U.S. Patent Publication No. 2012/0276763

(Quezada) is directed to an inner receptacle unit rather than a plug-in wall cover piece and therefore is totally different than the current invention.

U.S. Pat. No. 3,297,886 (Danner) discloses an arrangement in which AC input power is obtained from a wired plug and supplied as output power to a 2-prong external electric device, which has nothing to do with the current invention's USB charger since USB did not exist at the time of the patent, in 1967.

U.S. Pat. No. 6,540,554 (McCarthy) discloses a desk top power station rather than a plug-in wall outlet application, and which only includes (1) AC outlets, and (2) communication receiving ports for a telephone, telex, or fax equipment line, which bear no relation to a USB charger, USB having not yet attained popularity at the time of publication in 2001, at which time the iPhone had still not come out.

U.S. Patent Publication No. 2009/0315509 (Wu) discloses a socket with a built-in power source, but not for a plug-in wall outlet cover. Also, the socket of Wu has an internal power source which is not the same as that of the current invention since it does not get AC power source via prongs inserted into a wall inner receptacle receiving means.

In comparison with the inventor's U.S. Pat. No. 7,318,653, the present invention provides substantial improvements including:

AA. The current invention permits people to easily replace an existing non-USB charger wall cover by permanently installing a wall outlet cover that not only has a USB charger and AC outlet, but also light for illumination, and that can still further have more than two functions added on top of USB charging and illumination.

BB. The invention provides a cheap and inexpensive way for all hotels, houses, and offices to carry out a modern remodel in order to provide USB chargers on wall outlets without the need to spend big money for built-in USB chargers and lights, utilizing the tiny wall outlet space to provide chargers that cannot be stolen when using anti-theft screws to permanently secure the wall outlet covers and chargers to inner receptacle kits.

CC. The current invention has a universal movable piece that uniquely can fit all different inner receptacle shapes and configurations.

DD. The current invention provides electricity delivery from home electricity to the USB charger without the need to touch a live wire, so it is simple and even kids can perform replacement of a plug-in wall cover.

EE. The current invention may have a built-in added function to bring people even more convenience, by adding one or more of an optional outlet device, electric device(s), LED light device, EL light device, fluorescent tube device, power fail light device, illumination device, WiFi device, Internet device, wireless router device, timepiece, motion sensor device, remote control device, Bluetooth device, video camera device, recording device, memory means, digital data storage means, power means, energy saving means, energy storage device, batteries, DC power means, conductive means, prong means, electric parts and accessories, optics means, reflective means, and optics light traveling means.

BRIEF DESCRIPTION OF THE DRAWINGS

FIGS. 1, 1-2, 1A, 1B, and 1C show preferred embodiments of a multiple function wall cover plate having a number of USB chargers and built-in light sources to offer illumination or show charging status, and which include a moveable piece to make one product fit all kinds of inner receptacle shape and construction under the wall cover plate.

FIGS. 2, 2A, 2B, and 2C show a preferred USB wall cover plate having 2 USB receiving ports and details of the construction of the back side, and in particular the relationship between the back base, and movable-piece that enables the wall outlet cover plate to fit both traditional (2 separated oval-like receptacles) and decorative (a 1-piece rectangular-shaped receptacle) inner AC outlet receptacle under the existing wall cover plate.

FIGS. 4A and 4B show application to a one piece rectangular-shape receptacle, with FIG. 3A also showing a 1 port USB charger and FIG. 4A showing a 2 port (FIG. 4) USB charger.

FIGS. 10-22 show preferred embodiments having an desired combination or different assortment of USB and light sources, the preferred multiple function wall outlet cover optionally including one or more (1) optional outlet device, (2) electric devices(s), (3) LED light device, (4) EL light device, (5) fluorescent tube device, (6) power fail light device, (7) illumination device, (8) WiFi device, (9) Internet device, (10) wireless router device, (11) timepiece, (12) motion sensor device, (13) remote control device, (14) Bluetooth device, (15) video camera device, (16) recording device, (17) memory means, (18) digital data storage means, (19) power means, (20) energy saving means, (21) energy storage device, (22) batteries, (23) DC power means, (24) conductive means, (25) prong means, (26) electric parts and accessories, (27) optics means, (28) reflective means, and/or (29) optics light traveling means.

Also, FIG. 22 shows a wire arrangement of the type discussed above and disclosed in the inventor's U.S. patent application Ser. Nos. 13/858,046, 13/863,073, and 13/870,253. Included in the wire arrangement of FIG. 22 are a built-in groove or ditch to accommodate wire wrapped around the housing or a foldable frame or hooks to cause the wire to coil with an opening or fix the wire on certain coils. One end of the wire includes a USB-plug which can be plugged into USB-receiving ports to provide electricity delivery from the USB charger to another electric device or digital data device, which may include a communication, consumer electric, or computer device.

DETAILED DESCRIPTION OF THE PREFERRED EMBODIMENTS

Figure 3A:
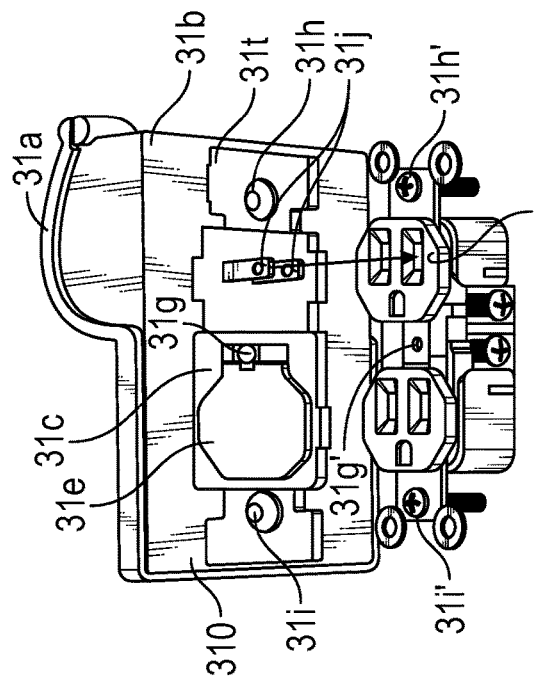
FIGS. 3, 3A, 4, and 4A show side and back views of another preferred design for a 2 major outlet receptacle, in which (1) FIGS. 3A and 3B illustrated application to 2 separated oval-like receptacles and (2)

The embodiment shown in FIG. 1 the multiple function wall cover (100) has a USB charger and built-in light for illumination or to show charging status, the wall cover (100) including a front cover (10a) and back base (10b) having central hole (10g) to allow a screw (not shown) to fasten the wall cover (100) on the inner receptacle center hole (10g') when the inner receptacle has the traditional two separated oval-shaped outlets (30e'). If the inner receptacle is a decorative-type receptacle (41f' or 62f), it has no central hole and therefore the wall cover needs to be fastened via the top (14h) and lower screw holes (14i). The wall cover (100) has one USB port (10d1) to allow a plug connected to another electric device to be inserted to charge the other electric device. An optics lens (10m) has one light bar (10n) to guide light from the two ends of the light bar into the optic lens (10m) and cause the optic lens (10m) to provide illumination or show a charging status. The movable-piece (10c) allows the current invention to fit both an inner receptacle having the traditional two separated oval shape outlets having central hole (30e') or a decorative receptacle having two outlets without central holes (41f').

As shown in FIG. 1-2 the wall cover has two USB ports (11d2) to allow people to charge two other electric devices at the same time. The current invention can have any number of USB ports from 1 to N (N is any number) depending on market requirements. The wall cover has a movable piece (11c) with an oval-shaped opening (11e) for the oval-like receptacle (31e', 60e') which allows the wall cover to become a universal wall cover capable of accommodating any kind of inner receptacle available from the market place.

As shown in FIGS. 1A, 1B, and 1C, the movable piece (13c) has a center hole (13g) and oval-shaped opening (13e) which can mounted on the wall cover of FIG. 1A. FIG. 1A is a back side view of the wall cover, in which one can see that the wall cover has one pair of prongs (12j) that are inserted into the inner receptacle (31e') when the movable piece (13c) is installed on the wall cover. When the movable piece (13c) is removed, the wall cover will fit other types of inner receptacle (41f'). The movable piece has an oval-shape opening (13e) that can only fit an inner oval-shaped receptacle (31e'), but when the movable piece (13c) is removed from the wall cover, the rectangular opening (14f) will be exposed so that the wall cover can fit the inner rectangular receptacle (41f'). As a result, the current invention provides an improvement over the previously-proposed multiple function wall cover in that the current invention wall cover is a universal type. However, it will be appreciated that the current invention also can have no movable piece and instead fit only one type of inner receptacle while still having a built-in USB charger and light means.

As shown in FIG. 1A, the wall cover has s movable piece (12c) with a center hole (12g) to allow a screw to fasten the wall cover on the inner oval-shaped receptacle (31e'). The wall cover also has top and bottom screw holes (12h) (12i) for attaching the wall cover to a decorative receptacle (41f') which has no central screw hole. However, if people feel more comfortable, it is possible to also fasten screws in the top and bottom screw holes when attaching the wall cover to an oval-shaped inner receptacle (30e'). The top and lower screw holes (12h) (12i) can be used for any kind of inner receptacle (31e', 41f).

As shown in FIG. 1C, the preferred wall cover has a rectangular opening (14f) for a rectangular inner receptacle (41f) and a prong (14j) to be inserted into the inner receptacle (41f) receiving means to complete an electric connection to get power. The wall cover does not require people to connect with the inner receptacle's wires, but rather simply requires that the prong (14j) be plugged into the inner receptacle's receiving hole, thereby enhancing safety by eliminating the need for people to cut the live wires and potentially come into contact with a high voltage and big current.

As shown in FIGS. 1A to 1C, the wall cover can fit different inner receptacles by simply moving a movable-piece (13c), which is a very good feature for a multiple function wall cover having a built-in USB charger and light means. This adds the advantage of convenience to the other advantages of the wall cover, which include not only allowing people to charge their communication, consumer electric, and computer devices from the wall cover, but also of offering an illumination function or showing a charging status.

As shown in FIG. 2, the wall cover has 2 USB ports to charge more than one electric device, as discussed above with respect to FIGS. 1, 1-2, 1A, 1B, and 1C. FIGS. 2A, 2B, and 2C also show details of how to use movable piece (22c) to adapt the wall cover from an oval-shaped inner receptacle (30e') to a rectangular-shaped inner receptacle (41f) and from the oval-shaped inner receptacle to the rectangular-shaped inner receptacle.

Figure 3:
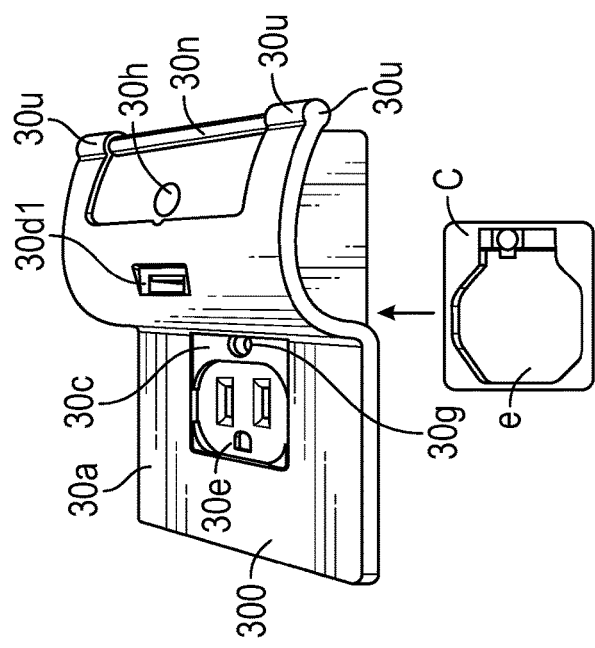

FIGS. 3 to 3A show a wall cover having 1 USB port (30d1), a center hole (30c), a top hole (30h), and a lower hole (30i). When the inner receptacle has an oval-shape (30e'), the movable piece (30c) needs to be on the housing (30a). The wall cover has a top and bottom half-groove (30u) to hold an optic-lens (30m) and light bar (30n), and the light bar has two light input ends (30v) to allow a light means (30L) to emit the light into the light bar (30n) cause the optics-lens (30m) to provide illumination or show a charging status. As shown in FIG. 3A, the prong (31j) is inserted into the oval-shaped receptacle (31e') receiving holes to get power from the wall outlet's inner receptacle. The wall cover has a central hole (31g) to allow screws to be fastened to the inner receptacle central hole (31g') so as to tightly attach the wall cover to the wall inner receptacle and to enable the wall cover opening (31e) to allow at least one of the outlets of the inner receptacle to show and be used by people. As shown in Figs. K, L, and M, the current invention also can have additional built-in outlets on the wall cover to make up for the one wall outlet that is used to get power via the wall cover's prong (31j).

Figure 4A:
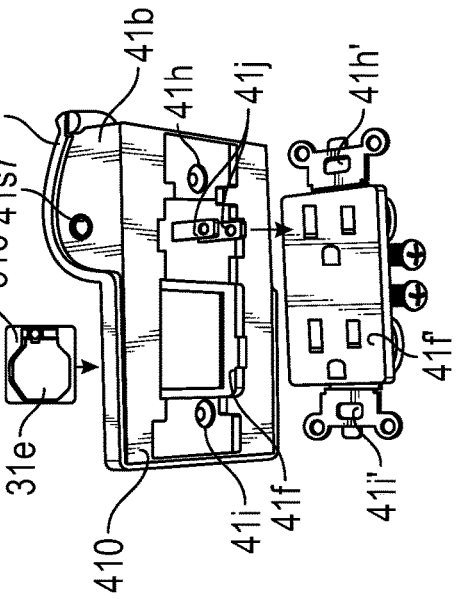
Figure 4:
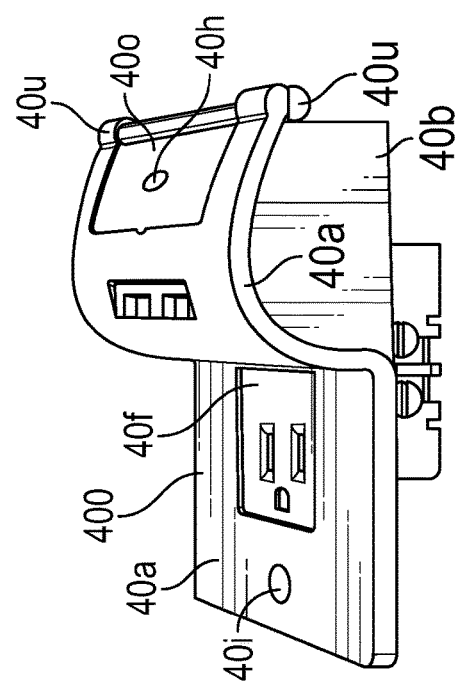

FIGS. 3A and 4A show the function of the movable piece (c), which is used to adapt the wall cover for oval-shape outlets to rectangular-shape outlets by adding or moving-away the movable piece. Other features shown in FIGS. 3A and 4A are the same as those shown in FIGS. 3 and 4.

Figure 5:
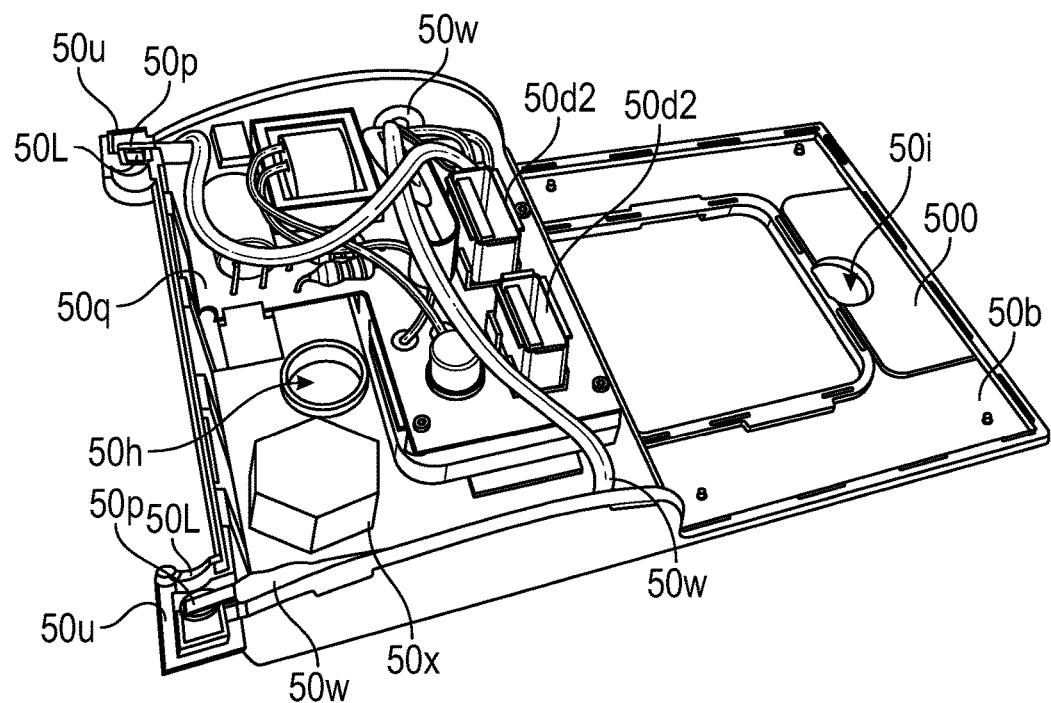
FIGS. 5 and 5A are perspective views an inner circuit, light means, USB ports, PCB, conductive wire, prongs, transformer or inverter, and control means in the form of a CDS photo cell installed within the back base and front cover of a preferred wall outlet cover.

As shown in FIG. 5, the wall cover has a base (50b) which has a top hole (50h) and lower hole (50i), and top parts having a compartment to allow installation of the USB charger and light means. The USB charger has a circuit (50q) which has a big PCB and a small PCB (50p) to install a transformer, resistor, capacitor, conductive wire, or related electric parts and accessories (50q). The current wall cover has 2 USB ports (50d2) also install in the circuit (50q) to allow charging of other electric devices when the other electric devices are plugged into the 2 USB ports (50d2). The circuit (50q) also has the small PCB (50p) on which SMT LEDs (50L) are preferably installed and which is connected to the circuit (50*q*) by electric conductive wire (50*w*) to offer desired functions of lighting, such as illumination or showing a charging status in which, for example, a red color illuminated LED means "lower power," a green color means "charging now," and a blue color means "fully charged," or in which more colors are included to show 10%-30%-50%-75%-100% charging status to let people see the charging status by using multiple color LEDs or color changing LEDs incorporated with a selected IC chip.

Figure 5A:
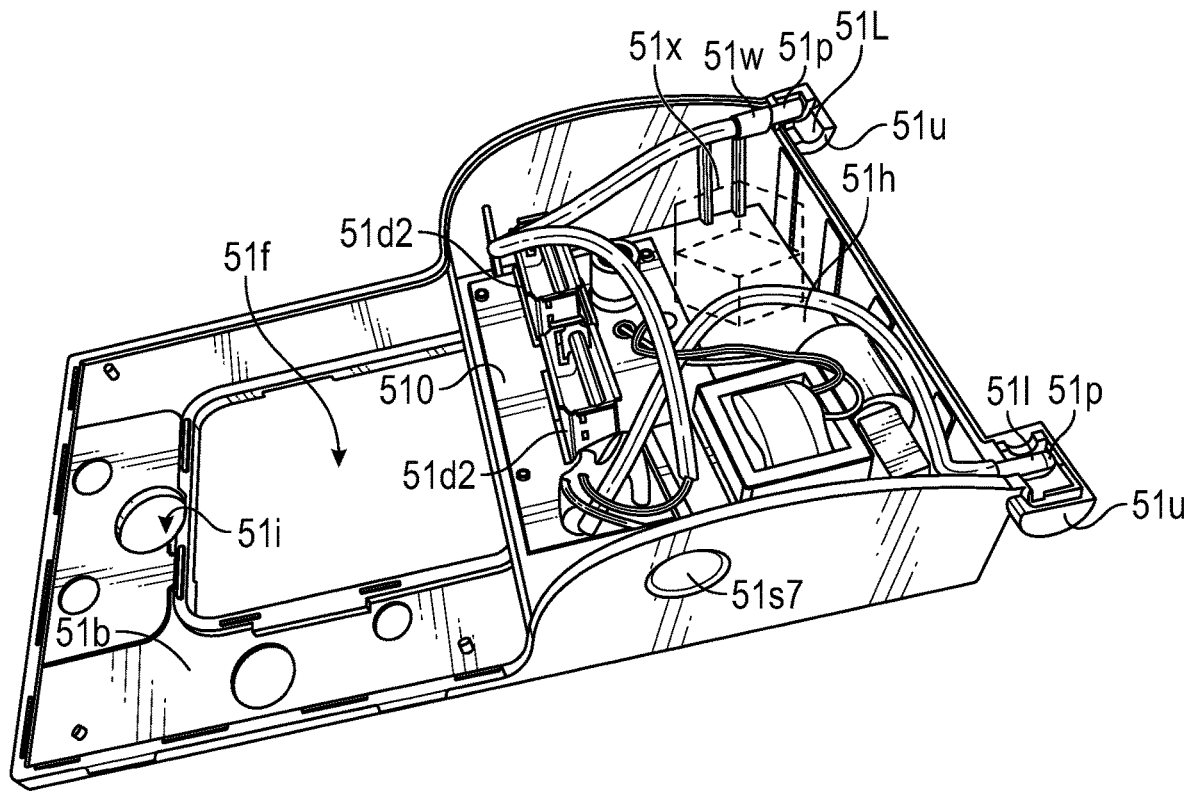
Figures 6, 6A, 6B:
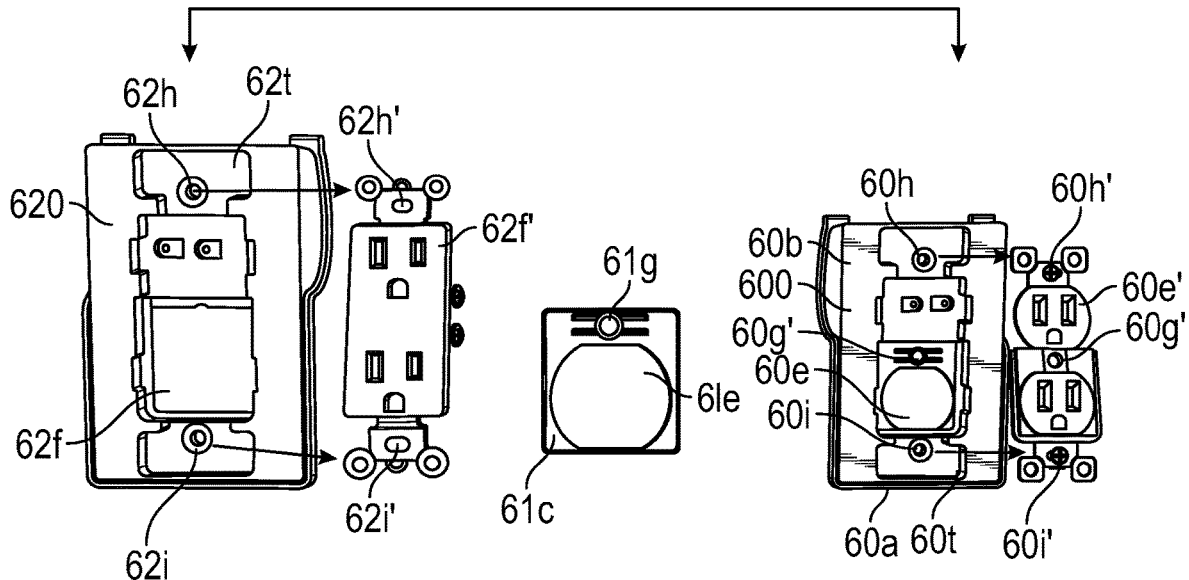
FIGS. 6, 6A, 6B, 7, 7A, and 7B show the relation between the moveable piece for preferred multiple function wall outlet cover plate and the existing inner wall receptacle for 2 different shapes, construction, and/or sizes.
Figures 7, 7A, 7B:
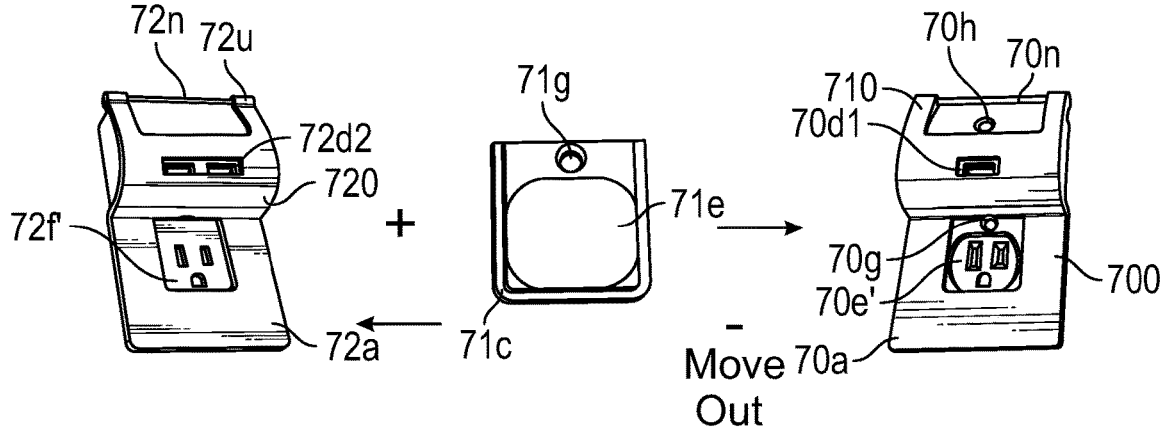

FIG. 5A shows the other side of LED (51L), small PCB (51*p*), and wire (51W), and additionally another controller (51*x*) which can provide the multiple function wall cover plate with more than two functions, the additional functions including one of an optional outlet device function and/or functions of an additional electric devices(s), LED light device, EL light device, fluorescent tube device, power fail light device, illumination device, WiFi device, Internet device, wireless router device, timepiece, motion sensor device, remote control device, Bluetooth device, video camera device, recording device, memory means, digital data storage means, power means, energy saving means, energy storage device, batteries, DC power means, conductive means, prong means, other electric parts and accessories, optics means, reflective means, and optics light traveling means, all of which are in addition to the USB charger and light means functions described above.

As shown in FIG. 5A, the built-in USB charger or light means, or other function, can have a desired controller selected from a switch (S), sensor (S1), remote control (S2), motion sensor (S3), Bluetooth wireless transmitter or receiver (S4), infrared remote control (S5), WiFi wireless controller (S6), photosensor (S7), CDS control (S8), or any other market available control means (S9). Any of these control means can be used with any of the illustrated embodiment of the invention.

FIGS. 6, 6A, 6B, 7, 7A, 7B, 8, 8A, 8B, 9, 9A, and 9B all show the same details discussed above, from different viewing angles.

Figure 8:
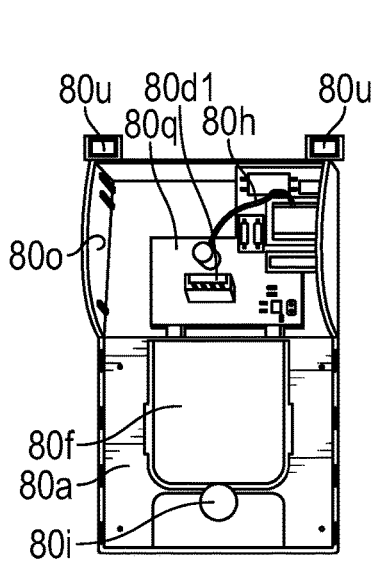
FIGS. 8, 8A, 8B, 9, 9A, and 9B show 1 port or 2 ports USB chargers for a multiple function wall outlet cover plate having a hinge type optics lens which has two ends to fit within two half-grooves o provide (1) light illumination, (2) charging status and/or (3) a cosmetic cover for inner screw holes, and/or (4) that further fits within another sensor, controller, wireless transmitting and receiving means, Bluetooth receiver for a wireless signal, remote control receiver, or WiFi related device to offer 3 or more additional functions.
Figure 8A:
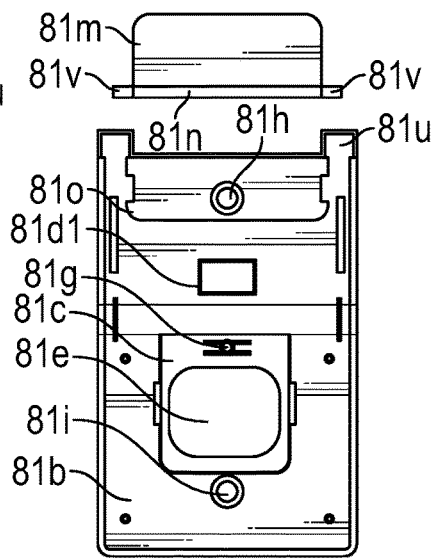
Figure 8B:
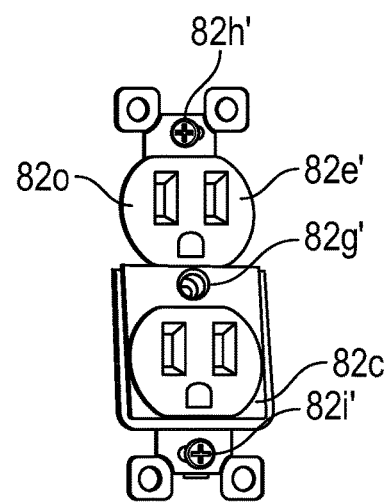
Figure 9:
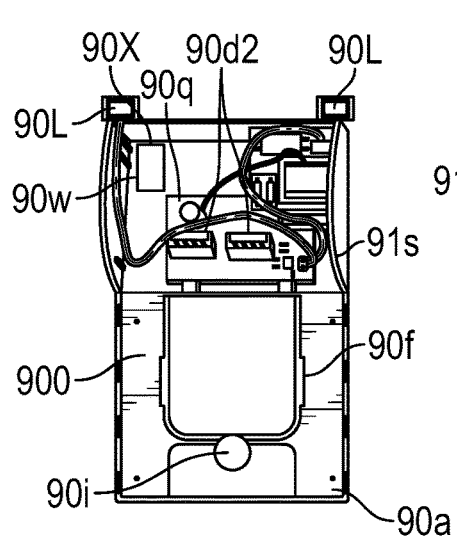
Figure 9A:
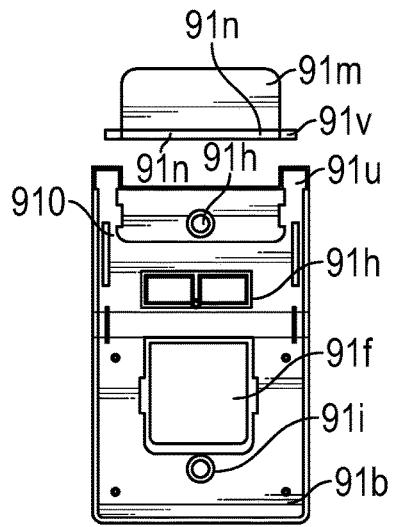
Figure 9B:
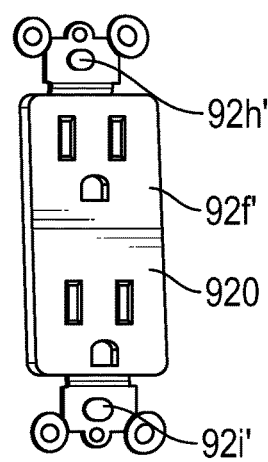
Figure 10:
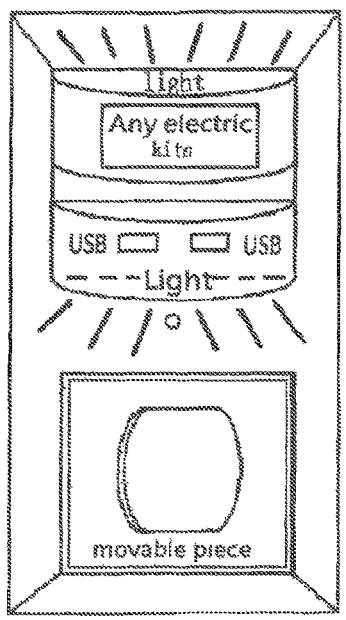
Figure 11:
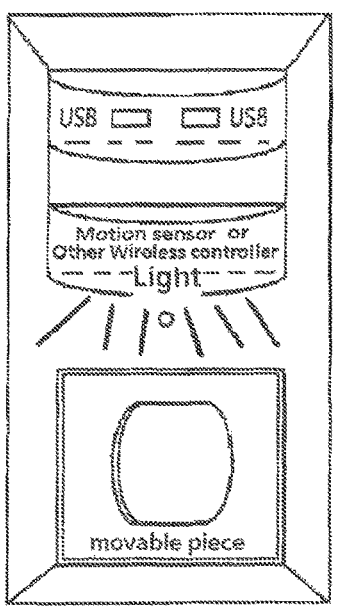
Figure 12:
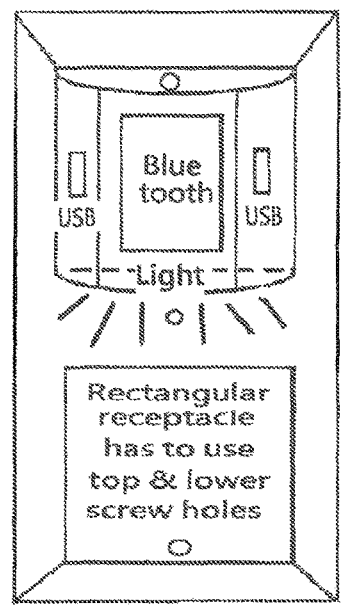
Figure 13:
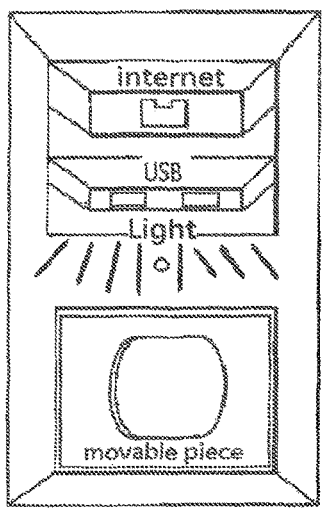
Figure 14:
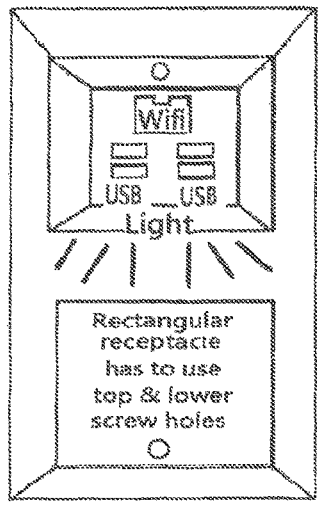
Figure 15:
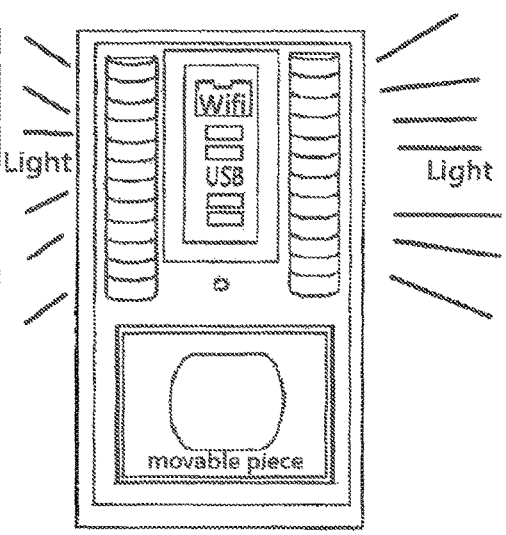

As shown in FIGS. 8, 8A, 8B, 9, 9A, and 9B, the USB charging circuit and light means are fit within the front cover (81*a*)(91*a*) and back base (80*b*) (90*b*), which are tightly sealed by clips and sonic sealing. The movable piece (81*c*) is fitted on the wall cover to adapt to different inner receptacles (82*e'*) and (92*f*). FIGS. 8, 8A, and 8B show oval-shaped inner receptacles, which need the movable piece to be installed on the wall cover to fit well. FIGS. 9, 9A, and 9B show rectangular shaped inner receptacles, for which there is no need to install the movable piece because the front cover and back base already have a rectangular opening to fit the rectangular inner receptacle.

The wall cover of the current invention can have any shape with any combination of desired functions in addition to the USB charger and built-in light means functions.

FIGS. 10-22 show preferred embodiments of multiple function wall outlet covers having any desired combination or different assortment of USB ports, light sources, and optional additional function devices, including an: (1) outlet device, (2) electric devices(s), (3) LED light device, (4) EL light device, (5) fluorescent tube device, (6) power fail light device, (7) illumination device, (8) WiFi device, internet device, (9) wireless router device, (10) timepiece, (11) motion sensor device, (12) remote control device, (13) Bluetooth device, (14) video camera device, (15) recording device, (16) memories means, (17) digital data storage means, (18) Power means, (19) energy saving means, (20) energy storage device, (21) batteries, (22) DC power means, (23) conductive means, (24) prong means, (25) electric parts and accessories, (26) optics means, (27) reflective means, (28) and/or optics light traveling means.

These embodiments each has (1) a central hole or (2) top and lower holes that enable use of a screw or screws to fasten the multiple function wall outlet cover on an existing wall outlet cover's inner kit's screw hole(s) to fix the multiple function wall outlet cover in position. The multiple wall outlet cover plate can replace an existing non-functional wall cover plate or overlay the existing wall cover because the electric delivery from the inner kit to the multiple wall cover is preferably made by conductive means in the form of a prong means, which may or may not have a ground pole.

The electricity delivery from the wall inner kit through the prong or prong(s) to the multiple function wall cover circuit supplies an AC electric signal to a multiple function circuit board to enable the multiple function wall outlet cover to provide multiple function under pre-determined functions by: (A) changing the AC electric signal to a DC electric signal to charge DC energy storage device such as an iPhone, iPad, smartphone, communication device, or consumer electric device, or (B) the outlet receiving means supplying the AC electric signal to an AC powered device such as a laptop computer or computer related parts or equipment such as s printer, scanner, fax machine or the like.

Figure 22:
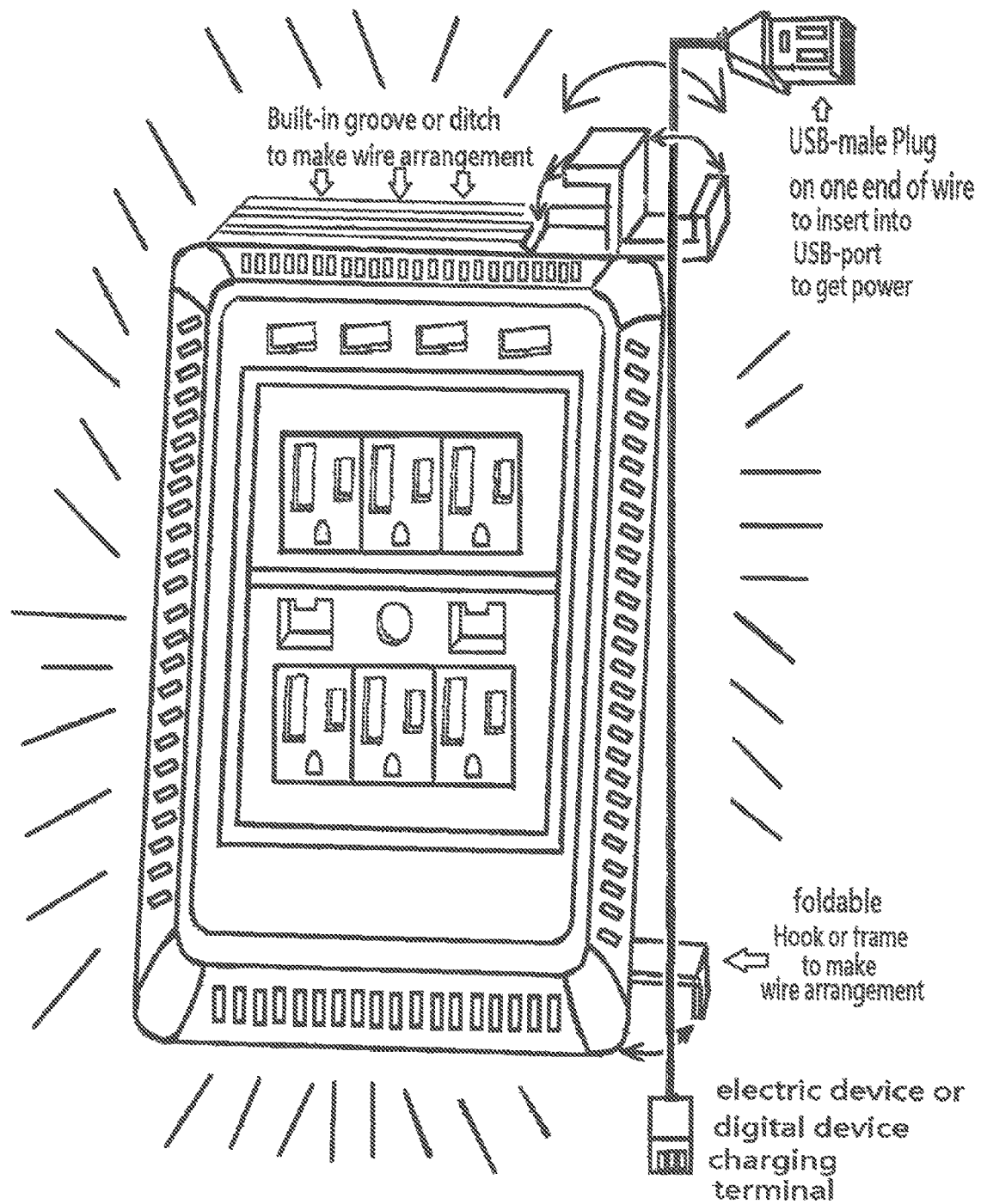
Figure 23:
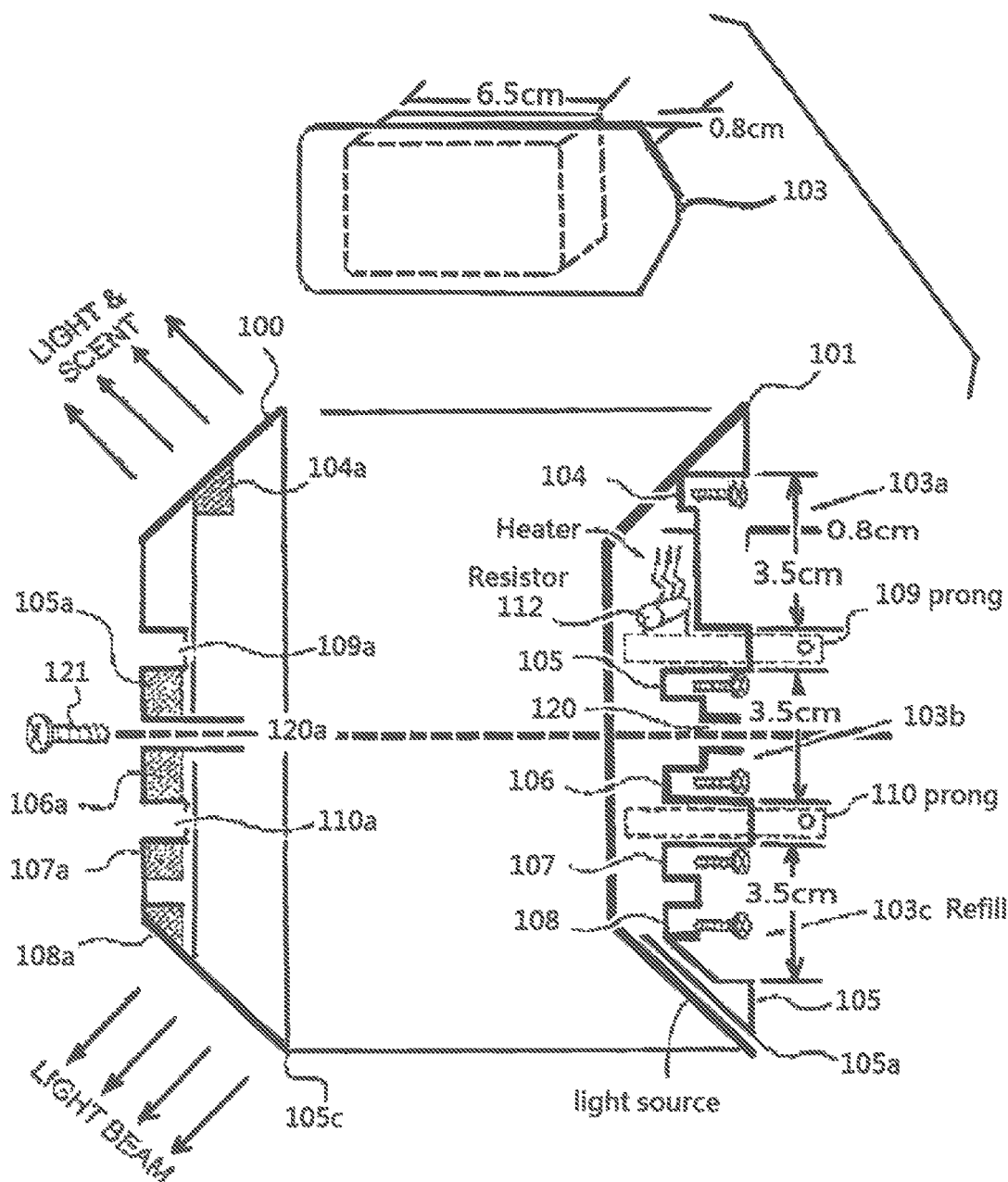
FIG. 23 is a side view showing the front cover and back base of the inventor's prior wall outlet cover, which includes: (1) an AC outlet receiving means, (2) a light source, and (3) an air freshener with a center screw to fasten and connect with a wall AC power source by prong means.

FIG. 22 shows a multiple functions wall cover plate having a bigger size than an existing wall cover so that it can cover a whole area of the existing wall cover and its respective hole on the surface to align with the inner receptacle's hole position to use (1) a central screw or (2) 2 side screws to fasten the multiple function wall cover plate to the wall outlet inner receptacle.

The multiple function wall outlet cover plate of the current invention is preferably not smaller than the existing wall cover plate. It will be appreciated that any size bigger than the existing wall outlet cover plate should still fall within the current invention scope, and that the multiple functions wall outlet cover plate may alternatively overlay the wall inner AC receptacle's receiving means depending on market requirements.

The multiple function wall outlet cover of FIGS. 10-22 also may be incorporated with a wire arrangement so long as there is existing space to accommodate a wire hold-means (not shown), The wire can be well arranged within the space to prevent a mess as described in the inventor's U.S. patent application Ser. Nos. 13/870,253 and 12/858,046. The multiple function wall outlet covers of FIGS. 10-22 may have any one or more of following 12 features and/or combinations of features:

1. The multiple function wall cover plate may be arranged to be installed on a wall outlets inner kit or receiving means and include at least one front cover and a back base assembled to the front cover to form the multiple function wall cover plate, the multiple function wall cover plate having a shape corresponding to that of the existing wall plate, wherein the multiple function wall cover plate is fastened by means of at least one of screw extending through the front cover, back base, and/or movable piece and prongs are arranged to supply electricity from the existing wall outlet receptacle when the prong is inserted into the at least one inner receptacle, the USB charger and optional light being installed within the front cover and back base together with the USB circuit, USB charger's receiving port(s), and related electric-parts or accessories, with at least one pair of the prongs or false prongs extending rearwardly from the back base for insertion into said wall existing outlet's inner receptacle and the USB charger's receiving port(s) being of any type, shape or construction capable of receiving a USB plug, prong, adaptor, or contact means of an external electric or digital data device(s) the at least one light source installed between the front cover and back base emitting light through the front cover or a contour, body or parts of the multiple function wall cover and thereby providing lighting effects such as illumination or indication of charging status, and the multiple function wall cover plate drawing power from the wall outlet's inner receptacle whenever the built-in prongs are connected to the existing wall inner receptacle to power a controller of the USB charger and light device as well as sensor means, a switch, a CDS, a motion sensor, a power fail sensor, a Bluetooth sensor, an IC, or any other electric or electronic control device through a transformer, inverter, or adaptor and related electric parts and accessories.

2. The multiple function wall outlet cover plate may further include at least one LED, electroluminescent element, fluorescent tube means, or other light means connected with an IC, sensor means or switch means, Bluetooth means, and/or remote control means to provide desired light effects with pre-determined functions or performance.

3. The multiple function wall outlet cover plate may include wire arrangement means permanently provided on the wall cover plate or an add-on design to ensure that any wire can be well arranged and stored.

4. The multiple function wall outlet cover plate may be overlayed on the existing wall outlet cover plate.

5. The multiple function wall outlet cover plate may include a USB charger having different output-currents ranging from 0.5 Amp to 1.0 Amp, 2.1 Amp, 2.4 Amp, 3.1 Amp, 3.4 Amp, 4.2 Amp, 4.4 Amp, or other current outputs to charge one or more than one communication, computer, consumer electric or digital data device at the same time.

6. The multiple function wall outlet cover plate may include other electric parts and accessories having at least one copper member arranged to supply electricity to the multiple function wall outlet cover plate's circuitry, including appropriate controlling means for different functions, and also to supply the electricity to the light means, as well as optionally to at least one added electrical device.

7. The multiple function wall outlet cover plate may have one movable piece which can be added onto the housing to fit existing 2 outlet, generally oval inner receptacle shapes, or removed to fit a decorative rectangular one piece wall outlet inner receptacle shape.

8. The multiple function wall outlet cover plate may have a variety of shapes and constructions of receiving means in the form of AC outlets which receive an AC input current and offer the same current as an output current to other electric or digital data devices, and the AC outlets or USB charger's receiving ports may have conductive or copper means connected to the existing receptacle by prongs, the conductive means selected from the group consisting of wires, metal materials, solder, resilient conductive means, and combinations of wires, metal material, solder, or resilient conductive means.

9. The multiple function wall outlet cover plate may have dimensions of 12-24 cm by 6-18 cm and more than two functions, of which the more than two function may be implemented by one or more of the following: an optional outlets device, electric devices(s), LED light device, EL light device, fluorescent tube device, power fail light device, illumination device, WiFi device, Internet device, wireless router device, timepiece, motion sensor device, remote control device, Bluetooth device, video camera device, recording device, memory means, digital data storage means, power means, energy saving means, energy storage device, batteries, DC power means, conductive means, prong means, electric parts and accessories, optics means, reflective means, and optics light traveling means.

10. The multiple function wall outlet cover plate may further include at least one front cover and a back base assembled to the front cover to form the multiple function wall outlet cover plate, the multiple function wall outlet cover plate having a shape corresponding to that of an existing wall plate, wherein the multiple function wall outlet cover plate is fastened by means of at least one screw extending through the front cover, back base, and/or movable piece to a wall inner receptacle's plate holder to replace of the existing wall plate, and at least one prong is arranged to supply electricity from the existing wall inner receptacle mounted in the wall, the multiple function wall outlet cover plate including at least one USB charger installed between the front cover and back base, with the at least one prong extending rearwardly from the front cover, back base, and/or movable piece for insertion into the existing wall inner receptacle, the front cover including USB charger receiving-means or an optional variety of receiving-means for inserting a USB-plug or other type of plug prongs, connector means, or adaptor means of an external device, and at least one light source also being installed between the front cover and the back base to emit light through a body, contour, or parts of the said multiple function wall outlet cover plate and thereby provide desired light effects whenever the at least one prong is connected to the wall inner existing receptacle and controlled by sensor means, switch means, power fail means, IC means, remote control means, Bluetooth means or other electric or electronic parts and accessories, the wall outlet cover plate further including at least one additional electrical device.

11. The at least one additional electrical device of the multiple function wall outlet cover plate may also be selected from the group consisting of: a. a fragrance dispenser; b. another light; c. an insect repeller; d. a timepiece; e. a motion sensor; f an infrared sensor; g. a Bluetooth electrical device controller. h. a WiFi or router or Internet device. i. video or audio devices and j. a wire arrangement means 12. The multiple function wall outlet cover plate may be a USB wall cover plate that includes at least one front cover and a back base assembled to the front cover to form the multiple function wall outlet cover plate, the multiple function USB wall cover plate having a shape corresponding to that of the existing wall plate, wherein the multiple function wall cover plate is fastened by means of a screw extending through the front cover, back base, and/or a movable piece to a plate holder of the existing inner receptacle, with at least one copper means in the form of prongs being arranged to supply electricity from the existing receptacle to at least one USB receiving means, the front cover including the USB charger's receiving-means for inserting a USB-plug of an external devices, and at least one light source being installed between the front cover and back base to emit light through a body or part of a housing of the multiple function wall cover plate and thereby provide desired light effects whenever the prongs are connected to the existing wall inner receptacle, with the light being controlled by a sensor, switch, power fail controller, IC, remote control, Bluetooth wireless controller or infra-red remote controller, motion sensor, and/or other electric or electronic parts and accessories, and the multiple function wall outlet cover including at least one additional electrical device.

The above discussed embodiments are not intended to limit the scope of the current invention. All alternatives, variations, equivalent functions, and minor changes will still fall within the scope of the current invention. For example, the number of prong means can be at least one pair under some special requirements and still can supply power to two receptacles depending on the design of the copper means/conductive means, and the copper means/conductive means also can have any configuration as long as it supplies electricity as necessary. Furthermore, as described above, the light means may include any available light means and installation without departing from the scope of the current invention. The attachment means, fastening means, and installation means also may be varied without departing from the scope of the invention.

I claim:

1. A multiple-function plug-in LED light, comprising:
   at least one LED for illumination visible on an optics lens or for status indication;
   at least one USB charger port for charging another product;
   at least one front cover and a back base assembled together, wherein;
   at least one prong supplies AC current to built-in AC-to-DC circuit and supplies a DC current to the at least one USB charger port and to at least one LED,
   the at least one USB charger port receives a USB plug arranged to deliver electrical current through a USB wire to said another product,
   the plug-in LED light further includes at least one of a sensor, switch, CDS, photosensor, motion sensor, power fail sensor, Bluetooth connector, remote control device, brightness or color changing control circuit, and integrated circuit.

2. A multiple-function plug-in LED light as claimed in claim 1, further comprising a movable piece adapted to enable the plug-in LED light to fit more than one type of plug-receiving wall receptacle.

3. A multiple-function plug-in LED light as claimed in claim 1, further comprising a wire arrangement structure for arranging and storing a wire connected to an AC outlet and at least one separate wire connected between the at least one USB charger port and the at least one external electric or digital data device.

4. A multiple-function plug-in LED light as claimed in claim 1, wherein the LED plug-in light includes LEDs having different colors to provide color changing or color selecting lighting effects.

5. A multiple-function plug-in LED light as claimed in claim 1, wherein the LED plug-in light includes LEDs having different colors to indicate different charging status.

6. A multiple-function plug-in LED light as claimed in claim 5, wherein said plug-in LED light has multiple USB ports supplied with said DC output current, and said DC output current is selected from 1.0 Amp, 2.1 Amp, 2.4 Amp, 3.1 Amp, 3.4 Amp, 4.2 Amp, 4.4 Amp, and more than 4.4 Amp.

7. A multiple-function plug-in LED light as claimed in claim 1, wherein an electrical conductor, said AC-to-DC circuit, and/or a DC-to-DC circuit connected to said at least one prong supplies power to said at least one USB charger port, an LED circuit, and/or an additional function-providing device.

8. A multiple-function plug-in LED light as claimed in claim 1, further comprising a movable piece having an oval shaped opening and at least one screw hole opening for adapting the LED plug-in light to at least one electrical receptacle having an oval shape, wherein the movable piece is removed from the wall cover plate to fit an electrical receptacle having a rectangular shape.

9. A multiple-function plug-in LED light as claimed in claim 1, wherein the LED plug-in light has at least one additional function-providing device installed within the LED plug-in light, said additional function-providing device including at least one of an (1) additional electrical outlet, (2) electrical device, (3) second color LED, (4) power fail light device, (5) illumination device, (6) WiFi device, (7) Internet device, (8) wireless router, (9) timepiece, (10) motion sensor, (11) remote control, (12) Bluetooth device, (13) video camera, (14) recording device, (15) digital data storage device, (16) power supply device, (17) memory device, (18) energy saving device, and (19) battery power bank device.

10. A multiple-function plug-in LED light, comprising:
    at least one LED light source;
    at least one prong arranged to be inserted into an AC wall outlet and supply power to an LED light source to (a) emit light through top, bottom, front or side walls or edges of the LED plug-in light, or (b) show a charging status;
    an AC-to-DC circuit that supplies a desired DC current to at least one USB port and the at least one LED light source,
    wherein the at least one USB port is arranged to receive a USB plug of an USB wire set to deliver electric current to at least one external electric or digital data device.

11. A multiple-function plug-in LED light as claimed in claim 10, further comprising an additional electrical device selected from a:
    a. fragrance dispenser;
    b. lighting device;
    c. insect repelling device;
    d. timepiece;
    e. motion sensor;
    f. infrared sensor;
    g. Bluetooth electrical device controller;
    h. WiFi device, router, or Internet device;
    i. video or audio device;
    j. wire arrangement device;
    k. a power fail light device;
    l. a power bank device; and
    m. a color changing, color selection, function selection, or brightness selection device.

12. An LED USB wall cover plate, comprising:
    at least one front cover and a back base assembled to form a housing of the USB wall cover plate, said USB wall cover plate having a shape corresponding to that of an existing wall plate,
    wherein the USB cover plate is fastened to an inner wall electrical receptacle by prongs extending through the back base, and includes a movable piece, said inner wall electrical receptacle having at least one AC outlet;
    at least one prong of the wall cover plate arranged to be inserted into the AC outlet to supply power to at least one AC-to-DC circuit and at least one LED light source installed within the USB wall cover plate to offer illumination or a charging status indicator light, wherein the USB wall cover plate further includes at least one additional built-in device selected from:
    a. a motion or photo sensor;
    b. a power fail device;
    c. a color or brightness selection or adjustment device;
    d. a power bank to charge other products while unplugged from a wall outlet;
    e. a switch;
    f. a wireless connection or controller device;

g. an infrared or radio frequency remote control circuit;
h. a Bluetooth, Z-way, ZigBee, WiFi, or Internet connection device;
i. downloaded app software; and
j. a moveable piece that is added-on the wall cover plate to fit oval or rectangular receptacles.

\* \* \* \* \*